US00PP24667P2

(12) United States Plant Patent
Renault

(10) Patent No.: US PP24,667 P2
(45) Date of Patent: Jul. 22, 2014

(54) ***HYDRANGEA* PLANT NAMED 'RENDIA'**

(50) Latin Name: *Hydrangea paniculata*
Varietal Denomination: RENDIA

(76) Inventor: Jean Renault, Gorron (FR)

( * ) Notice: Subject to any disclaimer, the term of this patent is extended or adjusted under 35 U.S.C. 154(b) by 135 days.

(21) Appl. No.: 13/573,268

(22) Filed: Sep. 5, 2012

(51) Int. Cl.
*A01H 5/00* (2006.01)

(52) U.S. Cl.
USPC ..... Plt./250

(58) Field of Classification Search
USPC ..... Plt./250
See application file for complete search history.

(56) References Cited

U.S. PATENT DOCUMENTS

PP16,166 P2 * 12/2005 Van Huylenbroeck ..... Plt./250
PP21,778 P2 * 3/2011 Kraan ..... Plt./250

OTHER PUBLICATIONS

UPOV Pluto Citations for RENDIA Apr. 11, 2011.*

* cited by examiner

*Primary Examiner* — Wendy C Haas
(74) *Attorney, Agent, or Firm* — Penny J. Aguirre

(57) ABSTRACT

A new cultivar of *Hydrangea paniculata* named 'RENDIA', characterized by its oblong shaped panicles of flowers that emerge white in mid summer and change to pink as they mature, and finally change to red at the end of summer, its blooms that turn red relatively early in the season, its sterile flowers with sepals that are large in size, its reddish-brown flowering stems extending to the tip of the inflorescence, its compact and open mounded plant habit, and its leaves that develop red spots in late summer that increase in size in fall.

2 Drawing Sheets

Genus/species: *Hydrangea paniculata.*
Varietal denomination: 'RENDIA'.

BACKGROUND OF THE INVENTION

The present invention relates to a new and distinct cultivar of *Hydrangea paniculata* and will be referred to hereafter by its cultivar name, 'RENDIA'. 'RENDIA' represents a new deciduous shrub grown for landscape use.

The new *Hydrangea* resulted from a controlled breeding program that commenced in 1987 in Gorron, France. 'RENDIA' was selected as a whole plant mutation in Gorron, France in 2007. 'RENDIA' arose from crosses made in 2001 between unnamed proprietary seedlings of the Inventor. The seeds from the crosses were pooled and the specific parents are unknown.

Asexual reproduction of the new cultivar was first accomplished by softwood cuttings in May of 2007 by the Inventor in Gorron, France. The characteristics of this cultivar have been determined to be stable and are reproduced true to type in successive generations.

SUMMARY OF THE INVENTION

The following traits have been repeatedly observed and represent the characteristics of the new cultivar as observed on plant grown in Gorron, France. These attributes in combination distinguish in 'RENDIA' from other varieties of *Hydrangea* known to the Inventor.

1. 'RENDIA' exhibits panicles of flowers that emerge white in mid summer and change to pink as they mature, and finally change to red at the end of summer.
2. 'RENDIA' blooms turn red relatively early in the season; in late summer rather than fall.

3. 'RENDIA' exhibits panicles that are oblong in shape when mature.
4. 'RENDIA' exhibits a compact and open mounded plant habit.
5. 'RENDIA' exhibits sterile flowers with sepals that are large in size.
6. 'RENDIA' exhibits reddish-brown flowering stems to the tip of the inflorescence.
7. 'RENDIA' exhibits leaves with red spots developing in late summer that increase in size in fall.

'RENDIA' can be most closely compared to *Hydrangea paniculata* cultivars 'RENSUN' U.S. Plant patent application Ser. No. 13/694,363, Wims Red U.S. Plant patent application Ser. No. 13/987,209, and 'DVPpinky' (U.S. Plant Pat. No. 16,166). 'RENSUN' differs from 'RENDIA' in having inflorescences that mature pink in color rather than red and in rarely producing fertile flowers. 'Wims Red' differs from 'RENDIA' in inflorescences that turn red later in the season, in having inflorescences that are more conical in shape, and in having a greater proportion of fertile flowers. 'DVPpinky' differs from 'RENDIA' in having a proportion of fertile flowers, in having a more upright plant habit, in being taller in height, in having shorter pedicels, and in having inflorescences that are pyramidal in shape.

BRIEF DESCRIPTION OF THE DRAWINGS

The drawings presented are digital photographs taken of plants 3 years in age as grown in a garden in Gorron, France.

The photograph in FIG. 1 provides a view of 'RENDIA' in bloom in mid summer.

Figure 1:
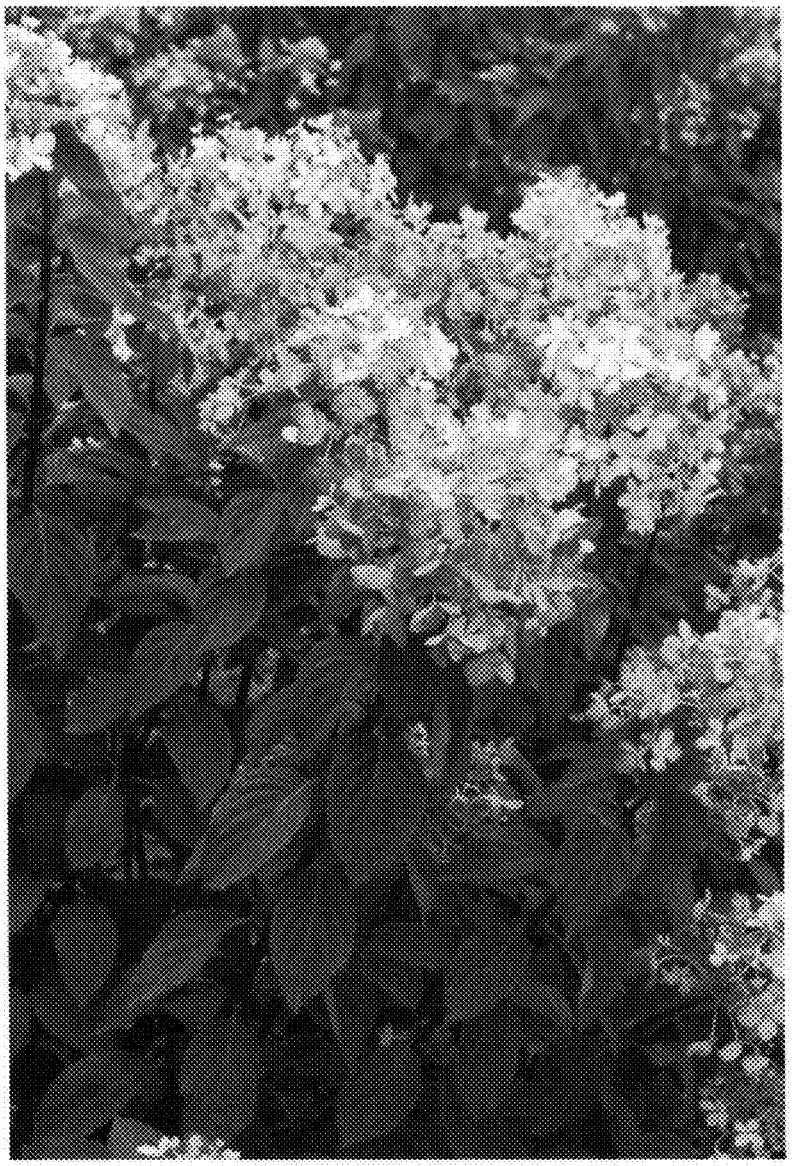
Figure 2:
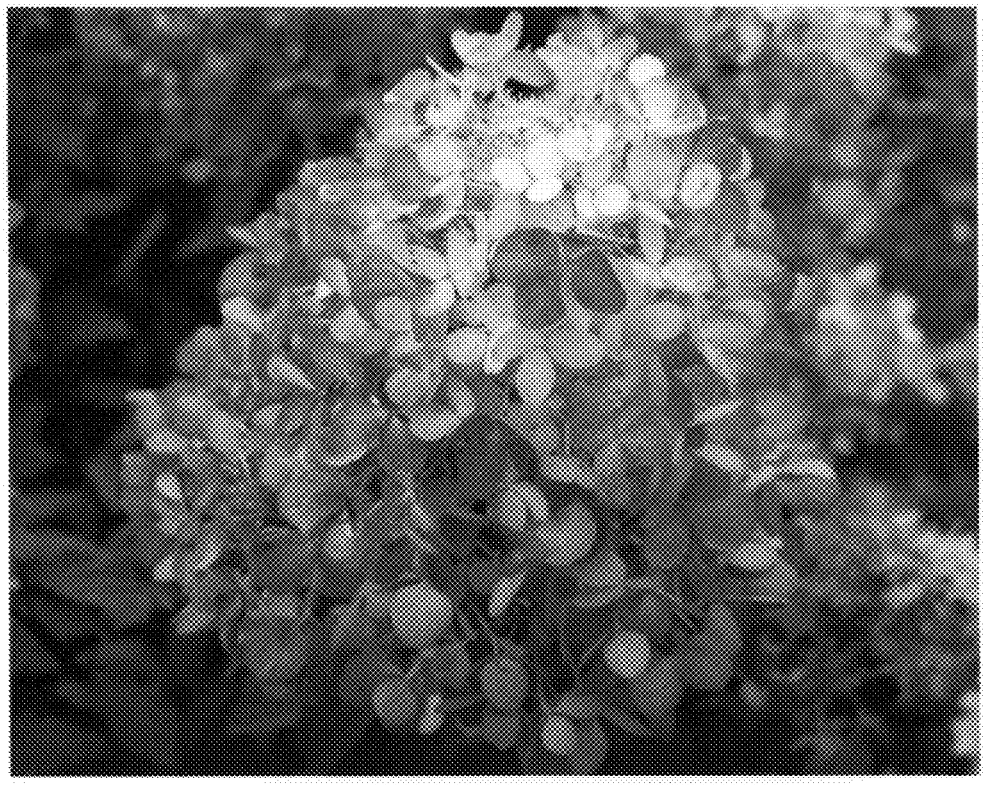

The photograph in FIG. 2 provides a close-up view of an inflorescence of 'RENDIA' in mid summer.

Figure 3:
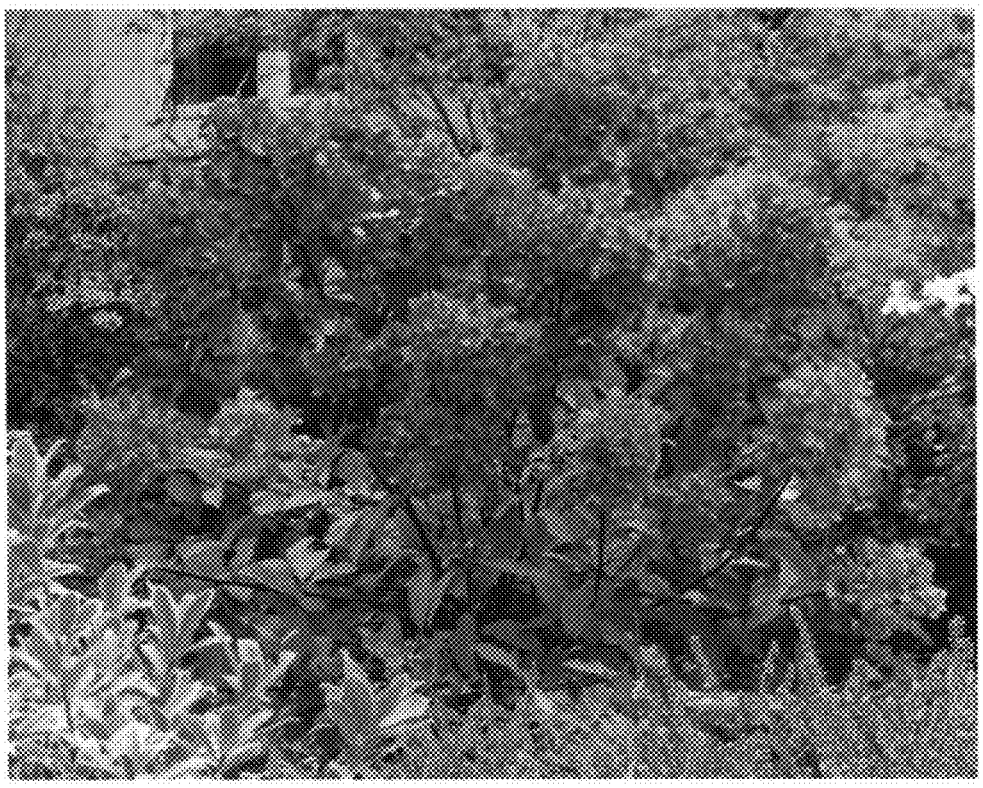

The photograph in FIG. 3 provides a view of a plant of 'RENDIA' in late summer. The colors in the photographs are as close as possible with the photographic and printing technology utilized. The color values cited in the detailed botanical description accurately describe the colors of the new *Hydrangea*.

BOTANICAL DESCRIPTION OF THE PLANT

The following is a detailed description of the new cultivar as observed on 3 year-old plants as grown outdoors in a garden in Gorron, France. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Blooming period*.—From mid July to the end of September in France.

*Plant habit*.—Compact, open mound.

*Height and spread*.—Reaches 1.5 m in height and 1.2 m in spread.

*Cold hardiness*.—At least in U.S.D.A. Zone 4.

*Diseases and pests*.—No susceptibility or resistance to diseases or pests has been observed.

*Root description*.—Fibrous.

*Propagation*.—Softwood stem cuttings.

*Growth rate*.—Moderate.

Stem description:

*Shape shape*.—Round, solid.

*Stem color*.—New wood 184A, mature wood 166A, old wood (dormant); 199B.

*Stem size*.—Average of 40 cm in length and 6 mm in diameter.

*Stem surface*.—Pubescent when young becoming glabrous.

*Internode length*.—Average of 3 cm.

*Branching*.—A single dormant stem will produce an average of 3 primary branches. Subsequent branching is determined by pinching; 2 stems develop per pinched node.

Foliage description:

*Leaf shape*.—Elliptic.

*Leaf division*.—Simple.

*Leaf base*.—Cuneate.

*Leaf apex*.—Primarily acuminate.

*Leaf venation*.—Pinnate, recessed, color 158D on upper surface and 158D on lower surface.

*Leaf margins*.—Serrated.

*Leaf attachment*.—Petiolate.

*Leaf arrangement*.—Opposite.

*Leaf surface*.—Glabrous on upper and lower surface.

*Leaf color*.—Newly formed leaves upper surface; 137C, newly formed leaves lower surface; 138B, mature leaves upper surface; 137B, mature leaves lower surface; 138B, spots develop in late summer into fall; 183A.

*Petioles*.—Average of 1.2 cm in length and 2 mm in width, sulcate in shape, 183A in color, stipules absent.

Inflorescence description:

*Inflorescence type*.—Terminal panicles that are oblong in shape and comprised of single sterile flowers and fertile flowers.

*Lastingness of inflorescence*.—Persistent with color lasting about 12 weeks.

*Inflorescence number*.—One per lateral or sublateral stem.

*Inflorescence size*.—Average of 20 cm in height and 15 cm in diameter.

*Flower number*.—An average of 250 sterile flowers per inflorescence and 370 fertile flowers per inflorescence.

*Flower fragrance*.—None.

*Flower aspect*.—Upright to outward.

*Flower size*.—Sterile flowers; an average of 4.5 cm in diameter and 0.5 cm in depth, fertile flowers; an average of 0.8 cm in diameter and 0.5 cm in depth.

*Flower buds*.—Sterile flowers; an average of 5 mm in length and 3 mm in width, globose in shape, NN115C in color, glabrous surface, fertile flowers; average of 5 mm in length and 3 mm in width, globose in shape, 157C in color, glabrous surface.

*Peduncles*.—Strong, extension of stem, average of 7 cm in length and 2 mm in width, 145B in color, surface is pubescent.

*Pedicels*.—Sterile flowers; moderate strength, an average of 2.5 mm in length and 1 mm in width, 157C in color and changing to 59D, surface is smooth and dull held between angles of 60°, fertile flowers; an average of 4 mm in length and 3 mm in length, moderate in strength, texture is smooth, dull.

*Fertile flowers*.—NN155C in color and changing to NN155C in color with sepals NN155C in color, an average of 4 mm in diameter and 1 mm in depth, rotate in shape, lasting about 7 days on the plant, not persistent on the plant (self cleaning).

*Sepals* (*sterile flowers*).—4, un-fused, not overlapping, rotate in arrangement, smooth, dull and glabrous on both surfaces, broadly elliptic to broadly ovate in shape, held nearly flat to slightly upwards when fully open, entire margin, apex is rounded to broadly acute, average of 2 cm in length and 1.8 cm in width, color upper and lower surface when newly opened in early summer, upper and lower surface; 157B, color when maturing in mid summer upper surface; 54A, color when maturing in mid summer lower surface 54B, color when mature in late summer, upper surface; 59C, color when mature in late summer, lower surface; 59B.

*Center* (*eye of sterile flowers*).—3 mm in diameter, 157C in color.

Reproductive organs (fertile flowers):

*Stamens*.—Average of 10, anther is about 1 mm in length and NN155C in color, filament is an average of 5 mm in length and NN155C in color, pollen is low in quantity and 160C in color.

*Pistils*.—Average of 3, average of 7 mm in length, 157B in color, style is an average of 2 mm in length, stigma is flattened on the of the style and 157B in color (newly opened blooms).

*Fruit and seed*.—None observed.

It is claimed:

1. A new and distinct cultivar of *Hydrangea* plant named 'RENDIA' as herein illustrated and described.

* * * * *